United States Patent [19]

Carbone

[11] Patent Number: 5,597,383
[45] Date of Patent: Jan. 28, 1997

[54] METHOD FOR CEMENTING INTRAMEDULLARY BONE PROSTHESIS

[76] Inventor: John J. Carbone, 7300 Old Harford Rd., Baltimore, Md. 21234

[21] Appl. No.: 164,764

[22] Filed: Dec. 10, 1993

Related U.S. Application Data

[60] Continuation-in-part of Ser. No. 945,622, Sep. 16, 1992, abandoned, which is a division of Ser. No. 777,726, Oct. 16, 1991, Pat. No. 5,340,362.

[51] Int. Cl.⁶ .............................. A61F 2/32; A61F 2/28; A61F 5/04
[52] U.S. Cl. .............................. 623/23; 623/16; 606/94; 606/92; 606/93; 606/95
[58] Field of Search .......................... 623/23, 16; 606/94, 606/92, 93, 95

[56] References Cited

U.S. PATENT DOCUMENTS

| | | | |
|---|---|---|---|
| 5,116,377 | 5/1992 | Skripitz et al. | 623/23 |
| 5,133,772 | 7/1992 | Hack et al. | 623/23 |

FOREIGN PATENT DOCUMENTS

| | | | |
|---|---|---|---|
| 0434604 | 6/1991 | European Pat. Off. | 623/23 |
| 3704089 | 8/1988 | Germany | 623/23 |

*Primary Examiner*—David Isabella
*Assistant Examiner*—Debra S. Brittingham

[57] ABSTRACT

An intramedullary bone prosthesis to be rigidly cemented into position in the femur, and also applicable to total knee and shoulder replacement operations, is provided as an improved surgical technique. The prosthesis is composed of a femoral head base, a femoral head post, a long femoral stem, a cement canal along its longitudinal axis, a spacer, a collar, and a distal restrictor. The prosthesis is placed into the prepared medullary canal. With collar in position, a bone cement injector is readily threaded on to the proximal portion of the cement canal. Cement is injected and subsequently travels down through the canal, through the spacer, and eventually exits openings at the bottom of the spacer. The distal restrictor plug halts downward cement travel, thus initiating an upward, substantially completely retrograde filling of the void in between the prosthesis and the cancellous bone wall. The cement reaches the collar or cement restrictor, thus proximally dislodging all air bubbles, blood, and blood products. Finally during curing, the cement injector, and excellent cement interdigitation is achieved.

11 Claims, 3 Drawing Sheets

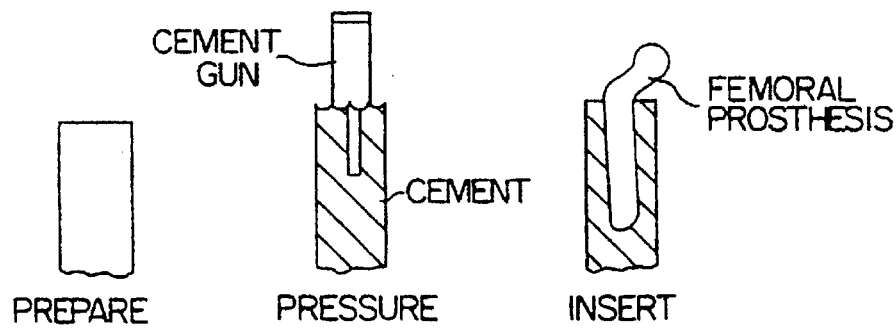
FIG. 1A PRIOR ART  
FIG. 1B PRIOR ART  
FIG. 1C PRIOR ART
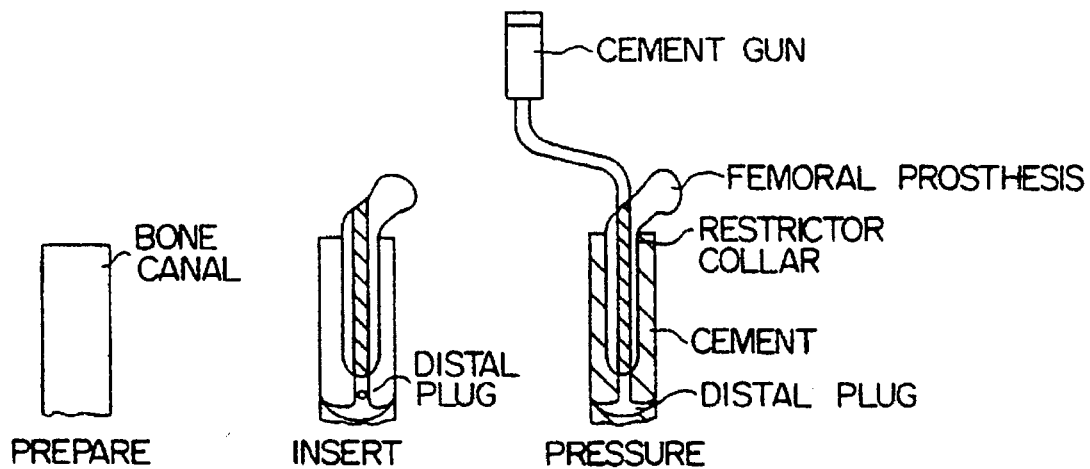
FIG. 2A  
FIG. 2B  
FIG. 2C

METHOD FOR CEMENTING INTRAMEDULLARY BONE PROSTHESIS

RELATED APPLICATIONS

This application is a continuation-in-part of U.S. Ser. No. 07/945,622, filed Sep. 16, 1992, now abandoned, which is a division of Ser. No. 07/777,726, filed Oct. 16, 1991, now U.S. Pat. No. 5,340,362.

BACKGROUND OF TEE INVENTION

This invention relates to prostheses, and more particularly to both the method and to a femoral intramedullary bone prostheses to be rigidly cemented into position on a person.

This invention relates to surgery and more particularly to the implanting of intramedullary bone prosthesis where an improved cementing technique may be utilized, especially in the femur.

BEST KNOWN PRIOR ART

The best known prior U.S. art is as follows:

| | | |
|---|---|---|
| 2,612,159 | 4,365,359 | 4,851,008 |
| 2,785,673 | 4,404,692 | 4,881,536 |
| 3,781,917 | 4,417,571 | 4,919,673 |
| 4,065,817 | 4,530,114 | 4,921,499 |
| 4,101,985 | 4,550,448 | 4,936,863 |
| 4,156,943 | 4,562,598 | 4,944,764 |
| 4,200,939 | 4,566,138 | 4,955,327 |
| 4,213,816 | 4,599,085 | 4,997,448 |
| 4,276,659 | 4,608,052 | 5,002,580 |
| 4,293,962 | 4,636,214 | 5,009,666 |
| 4,302,855 | 4,718,910 | 5,019,083 |
| 4,344,190 | 4,775,381 | 5,080,679 |
| 4,357,716 | 4,795,473 | 5,080,680 |

Femoral prosthesis operations may be broken down into two types: cement techniques and non-cement techniques. While both techniques have certain advantages and disadvantages, no one technique has proven to be ideal in the hip replacement category.

Both techniques involve amputating the femoral head at a designated point and preparing the medullary canal with some type of boring process. Non-cement techniques generally make use of a better prosthesis to medullary canal fit.

In the U.S. Pat. No. 2,612,159, Collison introduces a trochanteric plate which, when permanently placed on the femoral neck, can be joined to a femoral head. A similar scheme is proposed by Anderson in the U.S. Pat. No. 2,785,673 where the femoral head prosthesis is supported over a large area on the femoral neck.

The Kranz U.S. Pat. No. 4,562,598 teaches a prosthesis which is contoured to the medullary canal by means of an impervious prepreg member, while Mathys U.S. Pat. No. 3,781,917 discusses the anchoring of a femoral prosthesis through a screw placed through the collar of the prosthesis and into the outer corticalis.

In the U.S. Pat. No. 4,101,985, Baumann, et al teaches about a prosthesis with a special concave shape where small vibrations are taken care of by a threaded bolt attached to the prosthesis.

The Grimes U.S. Pat. No. 4,795,473 discloses a side plate device which results in an extramedullary prosthesis, while the Hofmann U.S. Pat. No. 4,936,863 shows a prosthesis which is enlarged for a tight fit after it has been introduced into the medullary canal.

U.S. Pat. No. 4,530,114, to Tepic, attempts to produce a prosthesis which seeks to emulate the characteristics of original bone stress absorption by using tension cables and a compression bolt.

The Kampen, et al U.S. Pat. No. 4,608,052 uses an integral attachment surface to let bone tissue grow into and thus better secure the prosthesis device. Similarly, Collier in U.S. Pat. No. 4,156,943 produces an orthopedic prosthesis which meets smoothness constraints of articulating bone joints yet contains pores ranging from 100 to 500 micrometers which are suitable for tissue growth.

Cementing techniques basically follow the same pattern. The medullary canal is prepared, a distal restrictor plug is inserted, cement is applied and pressurized, the prosthetic device is inserted, and the device is kept stationary until the cement has cured.

Some emphasis has been placed on developing better bone cements for these applications. The most typical and apparently effective bone cement is that composed of a polymethylmethacrylate polymer, usually liquid at temperatures above 45 degrees Celsius, but solid at body temperatures.

The Draenert U.S. Pat. No. 4,718,910 teaches a bone cement with a large surface provided to the implant but is characterized especially by exceptional mechanical strength. In the U.S. Pat. No. 4,200,939, Oser discusses a biocompatible, preformed, thermoplastic polymer other than the common polymethylmethacrylate type.

Intramedullary plugs of different varieties are used in cementing techniques. Emphasis is placed on obtaining a plug with the smallest chance of migration down the medullary canal. Migration leads to loss in cement pressurization and poor cement interdigitation. The Hardinge U.S. Pat. No. 4,276,659 discusses a hemispherical plug with radiating leaves. Similarly, the Lee, et al U.S. Pat. No. 4,344,190 introduces the concept of a biodegradable medullary plug which helps to position the prosthesis distally is introduced. A second intramedullary plug which aids in distal centering of a prosthesis, but which relies on penetration by the prosthesis, and which keeps the distal end of the prosthesis from being cemented is discussed by Filer in the U.S. Pat. No. 4,997,448. Distal centering by means of a cylindrical plug is referred to by Eftekhar in the U.S. Pat. No. 4,404,692. Van Syckle, et al teach in their U.S. Pat. No. 5,009,666 about a plug made for the purpose of filling a void in a prosthesis and which insulates against cement penetration.

Agreed to by most orthopedic surgeons is the need for an even layer of bone cement in prosthesis operations. This is accomplished, as discussed by Nelson, et al in U.S. Pat. No. 4,417,571, by three spacers arranged in equilateral triangle position. A prosthetic device with spacers pre-attached is the subject of the U.S. Pat. No. 4,566,138 disclosed by Lewis et al.

Prosthetic devices are often pre-coated before touching the cement bed in a medullary canal. The purpose of this is simply to provide a stronger bond for the cement and the prosthesis. The Morris U.S. Pat. No. 4,213,816 teaches the use of an interfacial layer or substrate formed between the underlying structural component and the porous layer. The porous layer is discussed by Raab in U.S. Pat. No. 4,365,359, where the spraying or dipping into a polymethylmethacrylate substance is said to promote better tissue growth into the prosthesis.

The Kenna U.S. Pat. No. 4,550,448 discloses a porous coating composed of two layers of ball-shaped metallic particles which is suitable for tissue growth or cement applications. In the U.S. Pat. No. 4,599,085, Riess, et al teaches coating a prosthesis composed of a biocompatible metal and a particulate calcium phosphate ceramic with a layer of calcium phosphate.

Various cementing procedures have been developed to try to increase the interdigitation between the cement and its bonding surfaces. In the Noble, et al U.S. Pat. No. 4,881,536, a preformed collar of bone cement is formed on the prosthesis which subsequently plunges down on the cement bed and forms adequate back pressure throughout the cement. The Homsy U.S. Pat. No. 4,636,214 teaches the use of a precisely formed medullary canal which minimizes the needed amount of cement.

In the U.S. Pat. No. 4,065,817, Branemark, et al discuss a prosthesis with a tubular support with lateral openings, where only the points having openings get cemented to the bone tissue, while the other points are left alone for the ingrowth of bone tissue, while the Willert, et al U.S. Pat. No. 4,919,673 teaches the use of a guiding rod, threaded on to the cavity of the prosthesis, to help position, implant, and set a bone prosthesis in a bed of cement. A device which allow the prosthesis to be prepositioned in the medullary cavity before the application of the cement is discussed by Brown in the U.S. Pat. No. 4,357,716.

Various other ideas and adjustments regarding prostheses have been previously discussed in the prior art. An adjustable prosthesis where the means of adjustment involves and inductive magnetic field is taught in the U.S. Pat. No. 4,921,499. Similarly, a prosthesis which is vibrated into position by means of ultrasonic sound is taught in the U.S Pat. No. 5,091,083.

Stossel has modified a previous femoral prosthesis in the U.S. Pat. No. 4,944,764 to provide for better leg abduction and to reduce the incision size for prosthesis fitting. A hip prosthesis which prevents fracture and can be used in conjunction with the medullary nailing technique is discussed in the U.S. Pat. No. 4,775,381. The Johnson U.S. Pat. No. 4,851,008 teaches a prosthesis with an essentially stress free outer surface which has "T" shaped slots leading to a stress bearing subsurface.

OBJECTS OF THE INVENTION

It is an object of this invention to provide a novel method and apparatus for cementing an intramedullary bone prosthesis.

Another object of this invention is to provide a novel intramedullary bone prosthesis which may be permanently connected to a distal restrictor plug composed of compliant material capable of centering the distal tip and occluding intramedullary canal.

Still another object of this invention is to provide an intramedullary bone prosthesis which can be threaded on to a bone cement injector.

To eliminate all air bubbles, blood, and blood products by filling the void or cavity with cement in a substantially completely retrograde fashion is another object of this invention.

To constantly pressurize the cement as it is curing to ensure better interdigitation into the prosthesis and the adjacent cancellous bone wall, is still another object of this invention.

To eliminate the disaster of having a bone cement cure too quickly to properly position the prosthesis, is a further object of this invention.

To help control the toxic fumes emitted from a bone cement in the operating room, is another object of this invention.

And to provide an intramedullary bone prosthesis which is centered distally by means of a distal restrictor plug and proximally by means of at least one shim positioned in the critical zone is yet another object of this invention.

BRIEF DESCRIPTION OF THE DRAWINGS

These and other objects and attendant advantages of this invention will become more obvious and apparent from the following detailed specification and accompanying drawings in which:

FIGS. 1a, 1b, and 1c are schematics of the steps in the conventional way of inserting and cementing a prosthesis in a bone structure;

FIGS. 2a, 2b, and 2c, illustrate schematics of the steps of the novel way of this invention of inserting and cementing a prosthesis in a bone structure;

DESCRIPTION OF THE PREFERRED EMBODIMENTS OF THE INVENTION

Referring generally to FIGS. 1a, 1b, and 1c, there is shown schematically the procedure for inserting and cementing a prosthesis in a bone cavity, with the bone structure first being prepared with the cavity, the cement then is inserted into the cavity, and then the prosthesis is inserted in the cement.

In this invention, as shown in FIGS. 2a, 2b, and 2c, the bone structure is prepared with a cavity, the cement is positioned in the prepared cavity and bone cement is then passed through a canal in the prosthesis. This cement is then exited from the opposite end of the canal in a substantially completely retrograde fashion into the cavity to subsequently fill it. A pressure collar is placed over the near end of the canal.

Figure 3:
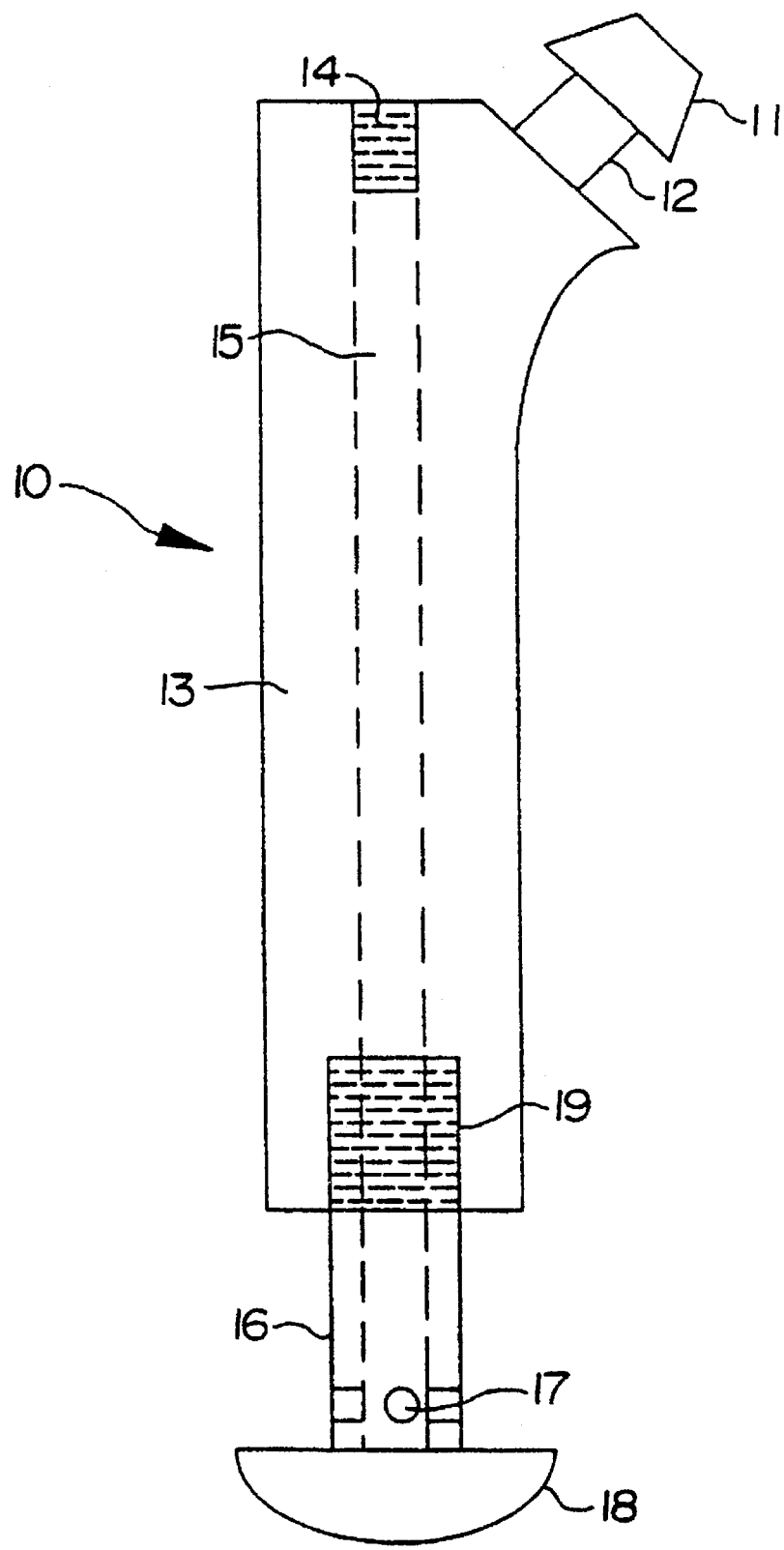
FIG. 3 is a front view of an intramedullary femoral bone prosthesis incorporating novel features of this invention.
Figure 4:
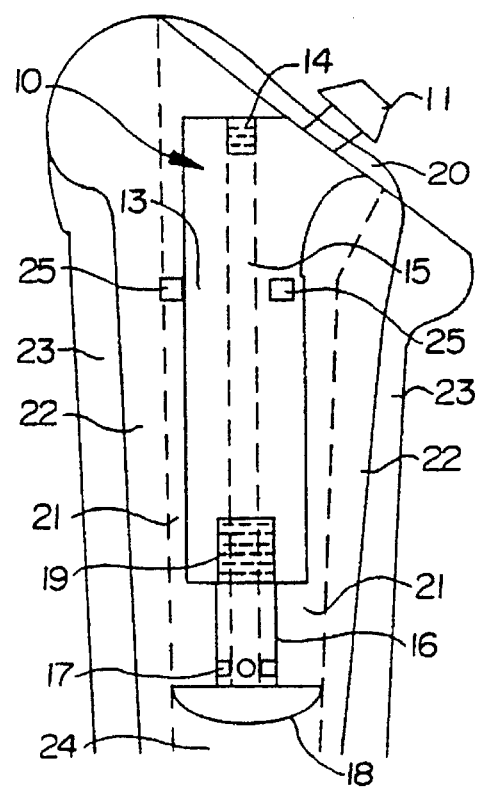
FIG. 4 is a front view of the intramedullary femoral bone prosthesis positioned for cementing inside the fumur.
Figure 5:
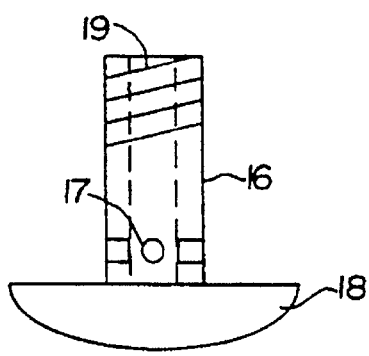
FIG. 5 is an enlarged front view of a spacer and distal restrictor plug of the intramedullary femoral bone prosthesis of FIG. 3.
Figure 6:
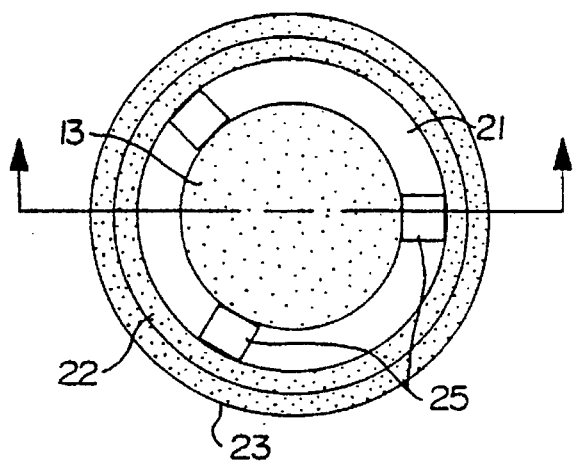
FIG. 6 is a cross sectional view of the intramedullary femoral bone prosthesis of FIG. 3 proximally centered into position by means of a plurality of shims.

Referring now to FIGS. 2a, 2b, 2c, and to 3 to 6 of the drawings, there is shown the preferred embodiment of the invention showing a femoral intramedullary bone prosthesis 10 as well as its position inside a medullary canal 24 (FIG. 4).

The femoral intramedullary bone prosthesis 10 consists of a femoral head base 11, a femoral head post 12, a femoral stem 13, and a distal plug 18 composed of polymethylmethacrylate or conventional plugs now in use. The distal plug 18 is joined to a spacer 16 composed of polymethylmethacrylate.

The distal plug 18 and spacer 16 are fixed to the femoral stem 13 by means of a set of threads 19. As bone cement is filled in, the possibility of distal plug 18 migration down the medullary canal 24 is eliminated and a predetermined space is kept between the femoral stem 13 and the distal plug 18.

Positioning the femoral intramedullary bone prosthesis 10 begins with joining it to a collar or cement restrictor 20 shown in FIG. 2. The collar 20 encompasses the entire mouth of the opening of the medullary canal 24 while slightly overlapping a neighboring cancellous bone 22 and possibly a dense cortical bone 23. The femoral intramedullary bone prosthesis 10 is then placed inside the prepared medullary canal 24.

Equal spacing between the femoral stem 13 and the wall of the cancellous bone 22 is achieved at the distal end by means of automatic centering in the distal plug 18. At the proximal end, this spacing is achieved by means of at least one cement shim 25 each of predetermined thickness and placed around the cancellous bone wall 22 in polygonal configuration. The placement of shim is shown in FIG. 4.

Once positioned, the femoral intramedullary bone prosthesis 10 is ready to receive the polymethylmethacrylate bone cement. Bone cement application begins by mating the threads on a bone cement injector to the threads 14 on the femoral stem canal 15. Once attached, bone cement is pushed down the femoral stem canal 15 until it reaches the top of the distal plug 18.

The bone cement then exits the femoral stem canal 15 through a plurality of openings 17 at the bottom of the spacer 16. In a substantially completely retrograde manner, the bone cement works its way up the open cavity 21 between the femoral stem 13 and the cancellous bone wall 22 of the medullary canal 24 until it reaches the collar or cement restrictor 20.

As the bone cement works its way up the open cavity 21, blood, blood products, and air bubbles are driven proximally and out of the medullary canal 24. As the bone cement fills the entire cavity 21, subsequent pressurization from the injecting device is added in a constant fashion, thus resulting in superior interdigitation of the cement to the femoral intramedullary bone prosthesis 10 and to the wall of the cancellous bone 22.

Obviously, many modifications and variations of the present invention are possible in light of the above description. It is, therefore, to be understood that within the scope of the appended claims the invention may be practiced than as specifically described.

What is claimed is:

1. A method for cementing a femoral intramedullary bone prosthesis to a bone structure, comprising the steps of providing a prosthesis including a stem, a distal restrictor, a separate spacer connecting the distal restrictor to the stem, apertures disposed in the spacer next to the distal restrictor and a canal in the prosthesis communications with the apertures, inserting the prosthesis in a prepared bone cavity, positioning the apertures at a distalmost end of a remaining unfilled space in the bone cavity defined between the prosthesis and the bone structure, introducing bone cement through the canal to cause the bone cement to enter the remaining unfilled space through the apertures and filling in a substantially completely retrograde manner the remaining unfilled space with the bone cement introduced through the canal.

2. The method as recited in claim 1 and further including the step of restricting flow of the bone cement from the bone cavity.

3. The method as recited in claim 1 wherein said step of positioning includes positioning the spacer at the distalmost end of the remaining unfilled space.

4. The method as recited in claim 3 wherein said step of introducing includes causing the bone cement to enter the remaining unfilled space through the apertures directly above the distal restrictor.

5. The method as recited in claim 1 wherein said step of positioning includes centering the prosthesis in the bone cavity.

6. The method as recited in claim 1 wherein said step of introducing includes coupling a cement injector with the canal and introducing cement from the cement injector into the canal.

7. A method for cementing a prosthesis in a cavity of a bone structure, comprising the steps of providing a prosthesis including a stem, a distal restrictor, a separate spacer connecting the distal restrictor to the stem, apertures disposed in the spacer and a canal in the prosthesis communicating with the apertures, preparing a cavity in the bone structure, inserting a prosthesis in the cavity, positioning the apertures at a distalmost end of a remaining unfilled space in the cavity defined between the prosthesis and the bone structure, introducing cement under pressure through the canal to cause the cement to enter the cavity around the prosthesis through the apertures and filling the cavity in a substantially completely retrograde manner with the cement introduced through the canal.

8. The method as recited in claim 7 wherein said step of positioning includes positioning the spacer at the distalmost end of the remaining unfilled space.

9. The method as recited in claim 8 wherein said step of introducing includes causing the cement to enter the cavity directly above the distal restrictor.

10. A method of cementing a prosthesis to a bone structure comprising the steps of providing a prosthesis having a stem, a distal restrictor spaced from the stem, a separate spacer connecting the distal restrictor to the stem, apertures in the spacer disposed between the stem and the distal restrictor and a canal in the prosthesis communicating with the apertures;

preparing a cavity in the bone structure to receive the prosthesis;

positioning the prosthesis in the cavity with the distal restrictor disposed at a distal end of the cavity in spaced relation with the stem;

introducing cement under pressure through the canal to cause the cement to enter the cavity between the prosthesis and the bone structure through the apertures; and filling the cavity from the distal end of the cavity to a proximal end of the cavity in a substantially completely retrograde manner with the cement introduced through the canal.

11. The method as recited in claim 10 wherein the apertures are disposed in the spacer next to the distal restrictor and said step of introducing includes causing the cement to enter the cavity through the apertures in the spacer directly above the distal restrictor.

* * * * *